United States Patent [19]
Holmberg

[11] Patent Number: 6,135,960
[45] Date of Patent: Oct. 24, 2000

[54] HIGH-RESOLUTION, THREE-DIMENSIONAL WHOLE BODY ULTRASOUND IMAGING SYSTEM

[76] Inventor: Linda Jean Holmberg, 4524 Verone, Bellaire, Tex. 77401

[21] Appl. No.: 09/143,901

[22] Filed: Aug. 31, 1998

[51] Int. Cl.⁷ ........................................................ A61B 8/00
[52] U.S. Cl. ............................................................ 600/447
[58] Field of Search .................................... 600/443, 447, 600/449, 450, 494; 128/916

[56] References Cited

U.S. PATENT DOCUMENTS

| | | | |
|---|---|---|---|
| 4,694,434 | 9/1987 | Von Ramm et al. | 128/916 |
| 5,222,499 | 6/1993 | Allen et al. | 606/130 |
| 5,269,309 | 12/1993 | Fort et al. | |
| 5,357,964 | 10/1994 | Spivey et al. | 600/443 |
| 5,465,722 | 11/1995 | Fort et al. | |
| 5,484,842 | 1/1996 | Quistgaard | 128/916 |
| 5,487,052 | 1/1996 | Cordsen | |
| 5,490,120 | 2/1996 | Li et al. | |
| 5,563,949 | 10/1996 | Bahorich et al. | |
| 5,611,343 | 3/1997 | Wilson | |
| 5,615,171 | 3/1997 | Hildebrand | |
| 5,617,548 | 4/1997 | West et al. | |
| 5,617,862 | 4/1997 | Cole et al. | |
| 5,619,999 | 4/1997 | Von Behren et al. | |
| 5,623,928 | 4/1997 | Wright et al. | |
| 5,628,320 | 5/1997 | Teo | |
| 5,629,904 | 5/1997 | Kosloff et al. | |
| 5,638,821 | 6/1997 | Nakamura et al. | |
| 5,640,370 | 6/1997 | Hanafy et al. | |
| 5,644,085 | 7/1997 | Lorraine et al. | |
| 5,644,646 | 7/1997 | Du et al. | |
| 5,661,697 | 8/1997 | Swan et al. | |
| 5,673,697 | 10/1997 | Bryan et al. | |
| 5,690,111 | 11/1997 | Tsujino | |
| 5,690,113 | 11/1997 | Sliwa, Jr. et al. | |
| 5,697,372 | 12/1997 | Hughes | |
| 5,720,290 | 2/1998 | Buhler et al. | |
| 5,724,978 | 3/1998 | Tenhoff | |
| 5,741,317 | 4/1998 | Ostrow | |
| 5,779,641 | 7/1998 | Hatfield et al. | 600/443 |

OTHER PUBLICATIONS

Prasad, Manika, et al., Effects of Pore and Differential Pressure on Compressional Wave Velocity and Quality Factor in Berea and Michigan Sandstones, *SEG Geophysics*, vol. 62, No. 4 (Jul. Aug. 1997) pp. 1163–1176.

Liu, Shenyue, An Analytical Approach to Migration Velocity Analysis, *SEG Geophysics*, vol. 62, No. 4 (Jul.–Aug. 1997), pp. 1238–1249.

(List continued on next page.)

*Primary Examiner*—Marvin M. Lateef
*Assistant Examiner*—Maulin Patel
*Attorney, Agent, or Firm*—Edward P. Black

[57] ABSTRACT

This invention incorporates the techniques of geophysical technology into medical imaging. Ultrasound waves are generated from multiple, simultaneous sources tuned for maximum penetration, resolution, and image quality. Digitally recorded reflections from throughout the body are combined into a file available for automated interpretation and wavelet attribute analyses. Unique points within the object are imaged from multiple positions for signal-to-noise enhancement and wavelet velocity determinations.

This system describes gaining critical efficiencies by reducing equation variables to known quantities. Sources and receivers are locked in invariant, known positions. Statistically valid measurements of densities and wavelet velocities are combined with object models and initial parameter assumptions. This makes possible three-dimensional images for viewing manipulation, mathematical analyses, and detailed interpretation, even of the body in motion.

The invention imposes a Cartesian coordinate system on the image of the object. This makes reference to any structure within the object repeatable and precise. Finally, the invention teaches how the recording and storing of the received signals from a whole body analysis makes a subsequent search for structures and details within the object possible without reexamining the object.

20 Claims, 3 Drawing Sheets

OTHER PUBLICATIONS

Raeuchle, Sandra K., et al., Integrating 3–D Seismic Imaging and Seismic Attribute Analysis with Genetic Stratigraphy: Implications for Infield Reserve Growth and Field Extension, Budare Field, Venezuela, *SEG Geophysics*, vol. 62, No. 5 (Sep.–Oct.. 1997), pp. 1510–1523.

Tygel, Martin, et al., A Unified Approach to 3–D Seismic Reflection Imaging. Part I: Basic Concepts, Part II: Theory, *SEG Geophysics*, vol. 61, No. 3 (May–Jun. 1996), pp. 742–775.

Sheriff, Robert E., Understanding the Fresnel Zone, *AAPG Explorer*, Oct., 1996, pp. 18–19.

Roux, Rosanne M., Ship Shoal 91 Field, Offshore Louisiana Discovery and Development of a Stratigraphic Field, *SEG Geophysics*, vol. 52, No. 11 (Nov. 1987), pp. 1466–1472.

Vermeer, Gys J. O., Streamers vs. Stationary Receivers, 1997 Offshore Technology Conference, Houston, May 5–8.

Blangy, J P., AVO in Transversely Isotropic Media—An Overview, *SEG Geophysics*, vol. 59, No. 5 (May 1994), pp.775–781.

Tsvankin, Ilya, Nonhyperbolic Reflection Moveout in Anisotropic Media, *SEG Geophysics*, vol. 59, No. 8 (Aug. 1994), pp. 1290–1304.

Gaullier, V., et. al, Near Bottom Sedimentation Process Revealed by Echo–Character Mapping Studies, Northwestern Mediterranean Basin, *AAPG Bulletin*, vol. 82/Jun. 6, 1998, pp. 1140–1155.

Prather, B. E., et. al., Classification Lithologic Calibration, and Stratigraphic Succession Of Seismic Facies of Intraslope Basins, Deep–Water Gulf of Mexico, *AAPG Bulletin*, vol. 82/5A, May 1998, pp. 701–728.

Di Siena, James, et. al., Calibration of Seismic Response for 3–D AVO Analysis, GCSSEPM Foundation, $17^{th}$ Annual Research Conference, Stratigraphic Analysis, Dec. 8–11, 1996, pp. 73–85.

Montgomery, Scott L., Stewart Field Finney County, Kansas: Seismic Definition of Thin Channel Reservoirs, *AAPG Bulletin*, vol. 80/Dec. 12, 1996, pp. 1833–1844.

Montgomery, Scott L., Brady Unit, Rock Springs Uplift, Wyoming: Migration and Structural History, *AAP Bulletin*, vol. 80/Oct. 10, 1996, pp. 1535–1546.

Brown, David, 3–D Targets Elusive Yegua Sands, *AAPG Explorer*, May 1997, pp. 6–7.

Henry, Steven G., Zero phase can aid interpretation, *AAPG Explorer*, Apr. 1997, pp. 66–69.

Rhodes, John A., et. al., Jurassic Stratigraphy of the Wiggins Arch, Mississippi, GCASC, Transaction of the $43^{rd}$ Annual Convention, Shreveport, La. Oct. 20–22, 1993, pp. 333–334.

Alkhalifah, Tariq, Velocity Analysis for Transversely Isotropic Media, *SEG Geophysics*, vol. 61, No. 5, pp. 1550–1566.

Alkhalifah, Tariq, Transformation to Zero Offset in Transversely Isotropic Media, *SEG Geophysics*, vol. 61, No. 4, (Jul.–Aug. 1996), pp. 947–963.

Hilterman, Fred, et. al., Identification of Lithology in the Gulf of Mexico, *SEG The Leading Edge*, Feb. 1998, pp. 215–222.

Brown, Alistair R., Interpretation of Three–Dimensional Seismic Data, *AAPG Memoir 42*, $4^{th}$ Edition, 1996, 444 pages.

Tucker, Karla E. et. al. Geologic Investigation of Cross–Well seismic Response in a Carbonate Reservoir, McElroy Field, West Texas, *AAPG Bulletin*, vol. 82/Aug. 8, 1998, pp. 1463–1503.

Radovich, Barbara J. et. al., 3–D sequence Interpretation of Seismic Instantaneous Attributes from the Gorgan Field, *SEG The Leading Edge*, Sep. 1998, pp. 1286–1293.

Schroeder, Fred W. et. al., How Fold and Bin Size Impact Data Interpetability, *SEG The Leading Edge*, Sep. 1998, pp. 1274–1284.

Payton, Lynn, et. al., Interpretation of Incised Valley Using New 3–D Seismic Techniques: A Case History Using Spectral Decomposition and Coherency, *SEG The Leading Edge*, Sep. 1998, pp. 1294–1298.

Anderson, Brian S., et. al., Integrated interpretaion in the Deep water Gulf of Mexico: Examples from the TGS Phase 45 Deep Water Reconnaissance Program, GCAGS Transacions of the $47t^h$ Annual Convention, New Orleans, La. Oct. 15–17, 1997, 21–26.

Schwartz, Bernie, Integrated 3–D Field Study on Workstation Results in New Reserves in an Old Field—High Island 140,Offshore Texas, GCAGS Transactions of the $47t^h$ Annual Convention, New Orleans, La. Oct. 15–17, 1997, pp. 505–512.

Sheppard, Frank C., et. al., Redevelopment of the Deep Tuscaloosa Gas Trend: A 3–D Seismic Case History of Judge Digby Field; Point Coupee Parish, Louisiana, GCAGS Transacions of the $47t^h$ Annual Convention, New Orleans, La. Oct. 15–17, 1997, pp. 523–528.

Fagin, Stuart W., Seismic Modeling of Geologic Structures, Applications to Exploration Problems, *SEG, Geophysical Development Series*, vol. 2, 1991, 269 pages.

*Reservoir Geophysics*, ed. Robert E. Sheriff, SEG Investigations in Geophysics, vol. 7 1992, 400 pages.

Offset–Dependent Reflectivity—Theory and Practice of AVO Analysis, ed. John P. Castagna, et. al., SEG Investigations in Geophysics, vol. 8, 1993, 348 pages.

Amplitude Variation with Offset: Gulf coast Case Studies, ed. James L. Alen, et. al., SEG Geophysical Development Series, vol. 4, 1989, 126 pages.

HIGH-RESOLUTION, THREE-DIMENSIONAL WHOLE BODY ULTRASOUND IMAGING SYSTEM

FIELD OF THE INVENTION

This invention relates to the high-resolution, three-dimensional ultrasound imaging of live bodies or other objects, enabling imaging of the whole object or any selected portion of the object using multiple, tuned sources and multiple receivers.

BACKGROUND OF THE INVENTION

The present invention is an application of seismic techniques to medical imaging. A description of seismic art as currently practiced in geophysical oil and gas exploration will be followed by a discussion of weaknesses in current medical imaging technology. Certain geophysical and other terms are explained as follows:

1. Object is the word used to define the body being imaged in the lattice structure. It can apply to a human patient, an animal, a plant, or any specifically defined object which can be brought into the range of the lattice's field.

2. Acoustic Impedance Contrast or Reflection Coefficient is a way to calculate the amount of reflected sound energy and is a function of the contrast in density and wave propagation velocity.

3. Normal Move-Out is a velocity determination from and correction for changes in receiver offset from the source.

4. Gathers are groups of the traces from individual receivers.

5. A Brute Stack is a preliminary image of summed traces where assumptions, rather than interpretation of actual velocities, are used.

6. Isochrons form a map, measured in time, from the difference between two time surfaces, where one is subtracted from the other.

7. Isopachs are similar to Isochrons, but converted are to a distance difference from the time difference by using appropriate velocities.

8. Velocity Analyses are a method to display and interpret root-mean-squared velocities from interpretation and auto-correlation functions used on the gathers.

9. Constant Velocity Stacks are a series of images of the same plane where one velocity function has been used for the entire plane in each panel and progressively higher constant velocities in subsequent panels.

10. FK Filters are a mathematical method of noise reduction.

11. Noise is unwanted response and may be, but is not limited to, water disturbances, multiple reflections, diffraction curves, out-of-the-plane reflections, instrument malfunctions, random noise, and processing problems.

12. Stacking is a method of summation after gathers have been corrected for the horizontal displacement by normal move-out.

13. Migration is a mathematical means to move reflections to their proper place in three-dimensional space.

14. Cartesian Coordinate System is a referencing technique which identifies three orthogonal (each at right angles) axes, usually designated as x, y, and z. The center, or origin, of such a coordinate system is where each of the axes has a zero value (0,0,0).

Sound energy propagates as a three-dimensional wave, with primary, (or p-) waves, being manifested as successive compaction and rarefaction. If the energy travels through an anisotropic material, one with different p-wave velocities in different directions, the wave will not be spherical. When a sonic wave encounters a boundary between different materials, i.e. an abrupt change in density and wave propagation velocity, part of the energy is refracted through the boundary and part is reflected back. The greater the contrast between the materials at the boundary, the greater is the acoustic impedance, contrast or reflection coefficient the greater the percentage of sonic energy reflected back and the lesser the percentage of the energy refracted onward. At any acoustic boundary, the angle of incidence equals the angle of reflection. This is commonly represented by rays drawn perpendicular to the tangent of the wave.

The most significant advance in seismic art has been common depth point imaging recorded directly in digital form. Common depth point imaging is a data manipulation technique which is a summation of many signals from different receivers, correlating coherent wavelet responses of multiple source/receiver positions to a common reflection point. This summation has the effect of 1. enhancing the strength of the boundary reflection,
2. reducing random noise through destructive interference, and
3. interpreting root-mean-squared velocities.

Commonly, multiple seismic sources emit sound energy simultaneously. These arrays of sources can be tuned, by a combination of phase, frequency, and amplitude of the emitted sonic pulse, both theoretically and empirically, for maximum effective penetration and imaging of the target.

The received signals from individual sonic receivers, set in a varying array (for example, multiple and multi-mile, flexible cables of towed hydrophones), are grouped into gathers so that normal move-out and spatial corrections can be applied. This allows interpretation of a signal to correct coherent reflections from increasingly horizontally offset receivers. In this manner, the reception time of the reflected energy signals from the same point, imaged from multiple angles and distances, becomes very close to the same for all angles and offset distances for that common depth point. Therefore, when these individually, digitally recorded, corrected wavelet traces are added, or stacked, together, boundary reflections are enhanced by constructive interference while random noise undergoes destructive interference. Thus, the signal to noise ratio is significantly, even dramatically, improved for substantially better imaging.

Analyses of multi-directional velocity data, which includes changes in reflection amplitude versus increasing offset (AVO) can, in particular circumstances, provide direct information on material composition and even fluid or gas content. Successful distinctions have been made on the gas or water content of microscopic pores between sand grains because of different horizontal and vertical wave velocities.

The problems associated with data interpretation include the unknown properties of the material through which the energy is propagating and its therefore unknown propagation velocity. Common industry practice is to interpret wave propagation velocity, then to vary the velocities in the computer while simultaneously observing the effects upon the gathers and the stacked traces. If wave velocities were known beforehand to a close approximation, much of this could be automated for a quick brute stack. Velocity analyses are also used to reduce or eliminate multiple reflections and diffractions. When correct diffraction velocities are found, point sources, like faults and fractures, can be determined.

A variety of mathematical algorithms are used to migrate reflections to their proper place in three-dimensional space.

Resulting, processed seismic data loaded onto a computer, are configured to appear as closely and regularly spaced vertical planes in two directions, with time-horizontal planes, making a three-dimensional volume. Navigation or surveying carefully establishes the position of every receiver within an established coordinate system, and hence, the position of associated, underlying reflection points. An interpreter will usually map the shape of surfaces. From any arbitrary or interpreted surface, many parallel slices can be generated for a quick look at wavelet attributes above and below the selected surfaces. Wave attributes (like amplitude, phase, coherence, frequency, multi-directional interval velocities, and calculated values like Poisson's ratio) can be automatically added over specified windows along the surface, isochrons and isopachs automatically constructed between selected surfaces, volumes automatically calculated, various mathematical functions applied to any set of x,y,z data points (referenced to the origin) to enhance discontinuities or amplitude anomalies, or to edit out known extraneous or erroneous data. Any set of x,y,z data points can be used in a mathematical function, or contoured and overlaid, with any other set of x,y,z points, not necessarily of seismic origin. Displays can be shaped for depth and colored for an attribute like amplitude. In a three-dimensional volume display, selected phases can be repeatedly faded into translucency or transparency in real time. Displays can be in the variable intensity format commonly used in most current medical imaging or in the wiggle-trace/variable area format sometimes used in geophysical displays.

The current art of medical imaging cannot provide a detailed, computer generated, three-dimensional image of the whole body of a particular patient. The current art of medical imaging of any type lacks a useable, repeatable x,y,z coordinate system for the body as a whole. The current art lacks the capability to manipulate signal response/wavelet attributes in a rigorous and substantial manner.

Magnetic resonance imaging (MRI), as currently available, has the capability to provide detailed, three-dimensional images, but only of selected portions of the anatomy. There are several other limitations to MRI. These include:

1. A significant number of patients do not meet eligibility requirements because of particular man-made objects within their bodies;
2. An MRI of just one part of the body (e.g. head or heart) is slow (about 45 minutes). Patients with some medical problems may have difficulty remaining prone and still for that period;
3. The equipment is very expensive, large, and not easily or widely available in many areas;
4. Many people find an MRI to be intimidating, uncomfortable, and unpleasant,
5. Effects of long-term (especially repeated) exposure to powerful magnetic fields are unknown.

Ultrasound is an alternative medical imaging technology to MRI. However, the present state-of-the-art for ultrasound also has limitations, giving rise to a corresponding need for improvement. These include:

1. Images have a poor signal to noise ratio, with fuzzy reflections and grainy background;
2. There is no systemic correction of velocity variations within observed tissue structures, leading to poor image resolution and ambiguities in interpretation;
3. Aside from minor use of amplitude response and Doppler frequency changes, current ultrasound imaging systems have no ability to process for and make use of wavelet attribute analyses for determination of body/organ characteristics,
4. There is a strong dependence on operator skill;
5. Often, the scanning procedure for a patient is a lengthy one;
6. Medical ultrasound lacks a rigorous time-to-depth conversion using known propagation velocities for the body as a whole;
7. Only a small portion of the body can be imaged at once.

Radioactive imaging techniques are potentially harmful if used too often or at too strong an intensity

THE PURPOSES OF THIS INVENTION

1. Produce computer generated three-dimensional images of the whole body of a subject, animal, or other object, or any part thereof, which are of good quality, high resolution, repeatable, and locatable. Said images will be obtained at a reasonable cost, with the subject required to spend just a few minutes in a non-threatening, comfortable apparatus for data collection.

2. Reduce many equation variables to knowns or close first-pass approximations, and use detailed and statistically valid models for enhancing processing speed and efficiency.

3. Collect and process the data to allow for wavelet attribute analyses to gain additional, direct information about the state and interaction of internal details such as organs, fluids, and other tissues.

4. Allow for computer-automated scanning of selected internal structures, with specific search parameters, to pinpoint abnormalities and changes over time for an analyst's closer examination.

5. Provide a method and apparatus to model, in the computer, projected surgery or other significant treatments, to provide before, during, and after images of lengthy treatments or progressive changes.

6. Provide an overall body x,y,z coordinate system to locate internal details and to enhance repeatability of subsequent imaging for computer processing and imaging.

SUMMARY OF THE INVENTION

To meet the objects enumerated above, this invention provides for an ultrasonic imaging system.

Said imaging system makes use of a plurality of ultrasonic emitters which can be adjusted in phase and amplitude to produce a transmitted signal wavefront which is designed for the most useful balance of frequency, resolution, and effective penetration. This allows either general scans to image the entire object, or targeted scans to concentrate on any portion of the object.

This invention also utilizes a plurality of ultrasonic receivers, the signals from each of which are independently recorded directly in digital form.

The sources and receivers are locked into a fixed geometry by being mounted on a "lattice" which has the characteristics of being a carefully defined, three-dimensional support for the said sources and receivers. The lattice of this invention can be made to be reconfigured to different sizes, shapes, and volumes to accommodate a wide variety of objects for analysis. The most important features of the lattice are that the physical location of each transmit and receive element is known to a close tolerance, and that the lattice is composed of replaceable sub-lattice units. The lattice and object are usually immersed in a benign fluid for the actual data collection.

This invention establishes a Cartesian coordinate system within the object of the analysis, although other coordinate systems, such as but not limited to, polar coordinate systems are also possible. Such an x,y,z coordinate system is critical to computer processing of a volume of data. The invention method designates a 0,0,0 point at an easily recognized point in the body. From the 0,0,0 origin, a vertical (z) and horizontal (x,y) axes are defined by lines drawn between other, easily imaged points. [As an example, for a human body, the 0,0,0 origin might be the center of one of the lower vertebra, with the z axis the line between the center of the uppermost vertebra and 0,0,0. The x axis might be the intersection of a line perpendicular to the z axis with the 90 degree projection of the navel onto that axis. The y axis would be perpendicular to both the x and z axes. For other objects, the origin and axes would be differently defined.] Once an origin and axes are established as a central, whole body coordinate system, subsidiary coordinate systems can be established for convenience in working with just subpart of the object like a foot or wrist.

Using the coordinate system of this method, every point in the object can be specified and located. Surgical procedures can be planned in the computer for a particular patient's body. The computer can be set to search for anomalies from closely set parameters. For subsequent images, the computer can be set to search for changes over time in well defined and repeatable locations in a particular body.

This invention also provides methods for reducing the number of variables for the equations and for speeding computer processing of the data. Because the positions of sources and receivers are always fixed, the navigation variable is eliminated and becomes, therefore, a fixed quantity in the equations. Estimates of densities and multi-directional wave propagation velocities give initial acoustic impedance parameters. Model-based estimates also provide initial frequency filters and migration velocities. Individual body type models provide approximate locations for internal structures for additional filtering. Finally, a plurality of markers of known acoustic contrast or reflection coefficient impedance affixed to the body or object give absolute rather than relative reflection amplitude.

This invention also provides for the extraction of additional information from digitized data by utilizing deductions and inferences from the data processing sequences and analyses of the wavelet attributes of the subsequent, stacked and migrated reflection data. From the processing sequences, additional information may be gleaned using velocity analyses, constant velocity stacks, FK filter applications, diffractions (to locate point sources like fractures or other point discontinuities), and amplitude versus offset of coherent reflections in the gathers (which may allow for direct gas/fluid prediction).

In addition, wavelet attribute techniques identify amplitude variations along a designated surface, measure coherence of adjacent traces from autocorrelation windows, find frequency shadows, search phase volumes for discontinuities, and use calculated values such as Poisson's ratio to provide crossplots of such attributes with other types of non-acoustic data.

This invention provides the potential for historical analysis, over time, of subjects imaged in the apparatus discussed. Most imaging technologies consider only isolated portions of a subject. However, this method gathers data on the entire subject and the interactions of internal structures, which may be used for later analysis. [For example, if a patient were found to have malignancy, an analyst can reprocess the data tapes and examine other areas of the body for evidence of metastasis products. Any suspect locations can become the target for detailed analysis on subsequent scans of the same subject.] Using this historical capability, certain conditions can be monitored over time in great detail for evidence of changes and developments. For example, changes in the cardiovascular system or skeletal/muscle system can be computer-compared for quantitative and qualitative changes, under calculated, intended stresses, and over a span of time.

Finally, this invention provides the opportunity to view and to analyze internal structure interaction of organs within a body, in motion. Because the speed of sound through sea water is about 5000 feet/second, movement of organs or fluids within the body are far slower than sound or ultrasound waves. Movement of systems, like muscle, tendon, cartilage, and bone; or heart, lungs, and blood vessels, could be imaged like frames of a movie—but available for detailed computer analysis of their interaction.

DESCRIPTION OF THE DRAWINGS

Other objects, features and advantages of the present invention will become apparent from the detailed description of the invention that follows, when considered in light of the accompanying drawings, in which.

DETAILED DESCRIPTION OF THE DISCLOSURE

The lattice of this invention can be implemented by, but is not limited to, the following three styles of apparatus.

1. An open bar lattice is composed of a series of interlocking supports which form a three-dimensional grid. Arrays of sources and receivers on any bar are always configured in precisely known positions. The lattice can be immersed in tubs, swimming pools, or even in the ocean.

2. In another form, the lattice can be implemented as a series of solid, stacked rings, open or closed, which latch together, in one way only, into a cylinder or other shape. When assembled, the solid lattice would be watertight. The overall lattice size can be adjusted for children or adults, or made smaller or larger for specific needs. The closed, ring-latched lattice is filled with a benign fluid known to have minimal acoustic impedance contrast or reflection coefficient with the surface of the object for maximum energy refraction into the object. Arrays of sources and receivers are configured in the same position on every working ring in the lattice.

3. A shell apparatus is a hard shell with a series of short, extendable rods containing sources and receivers. The exact position of every rod in the shell is known and the amount of extension necessary for each rod to achieve contact with the object is closely measured. Using this implementation, shear waves, which cannot travel though a fluid and which have different propagation velocities and wavelet attributes than do p-waves, can be collected for comparison with p-waves.

Figure 1:
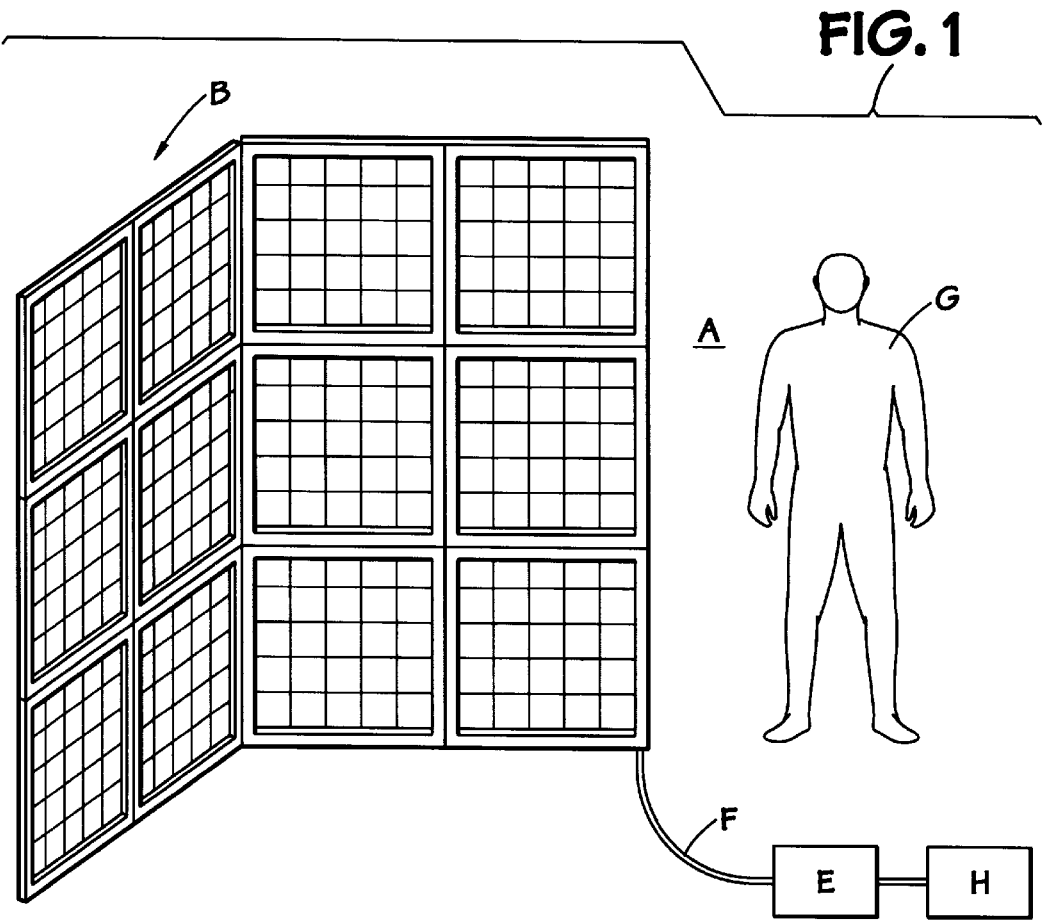
FIG. 1 is a representation of an open Lattice, including component panels, with its accompanying signal cables and control circuitry, also showing a figure (G) of an object to be imaged, in the field of the lattice, with the whole immersed in a benign fluid.

In the preferred configuration, (which is the first alternative discussed above), this invention will be implemented as an open lattice structure, as illustrated in FIG. 1, and immersed in water (A) or, optimally, a fluid (A) with minimal acoustic impedance with the skin or outer surface of the object. The framework (B), holds the receivers, and sources.

Sub-lattice panels (FIG. 2) containing arrays of sources (C) and/or receivers (D) lock together into an expandable lattice, planar or polygonal. Resulting lattice configurations may range from quite small to very large, from one plane to a complete enclosure. Sources and/or receivers have a fixed, known location on each sub-panel.

The signals from the sources and receivers are connected to the control system (E), through the signal cables (F). The lattice structure is immersed in a fluid. The object (G), is brought into the range of the lattice.

With the object in position, the scanning circuitry is activated. Selected groups of sources and receivers are activated in patterns, which change as the survey continues. Emitted frequencies may also be changed in a selected manner. A transmitted wave front is calculated to provide the maximum sound energy on the portion of the object to be examined, and created by selectively controlling the amplitude, frequency, and phase of each source. As the wavefront is generated, selected receiver channels are activated and the signals from each are recorded in digital form.

Laboratory measurements of densities and multi-directional wave propagation velocities on large numbers of samples of every type of material pertinent to the imaging process in the body are necessary to form statistically valid initial acoustic impedance parameters, and, hence, to reduce computation time significantly. Much testing develops the necessary initial frequency filters and migration velocity models. The closest of a large number of preliminary, physiological models are modified by a comprehensive patient history to satisfy physical anthropological assessments. Detailed physical measurements of subjects to be analyzed refine the models further. A number of markers of known acoustic impedance are affixed to the body and, in some cases, swallowed or otherwise introduced internally, for absolute rather than relative reflection amplitude. Other acoustic markers note areas of concern or potential surgical incision.

Figure 3:
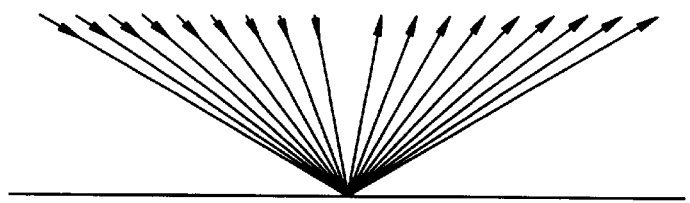
FIG. 3 is a simple ray diagram, illustrating the fact that sonic waves reflect (i.e. the angle of reflection equals the angle of incidence).

The multiple, coordinated sources emit the ultrasound signal. The wavepaths, represented by rays perpendicular to the tangent of the wave, from a number of sources, are shown in FIG. 3 as they each reach a single point (one of many) from a different angle. The angle of reflection equals the angle of incidence, so the signal from each source is received by a different receiver. The same is true for other, imaged points. Each receiver has its amplitude and time data recorded with its coordinate system location.

Figure 4:
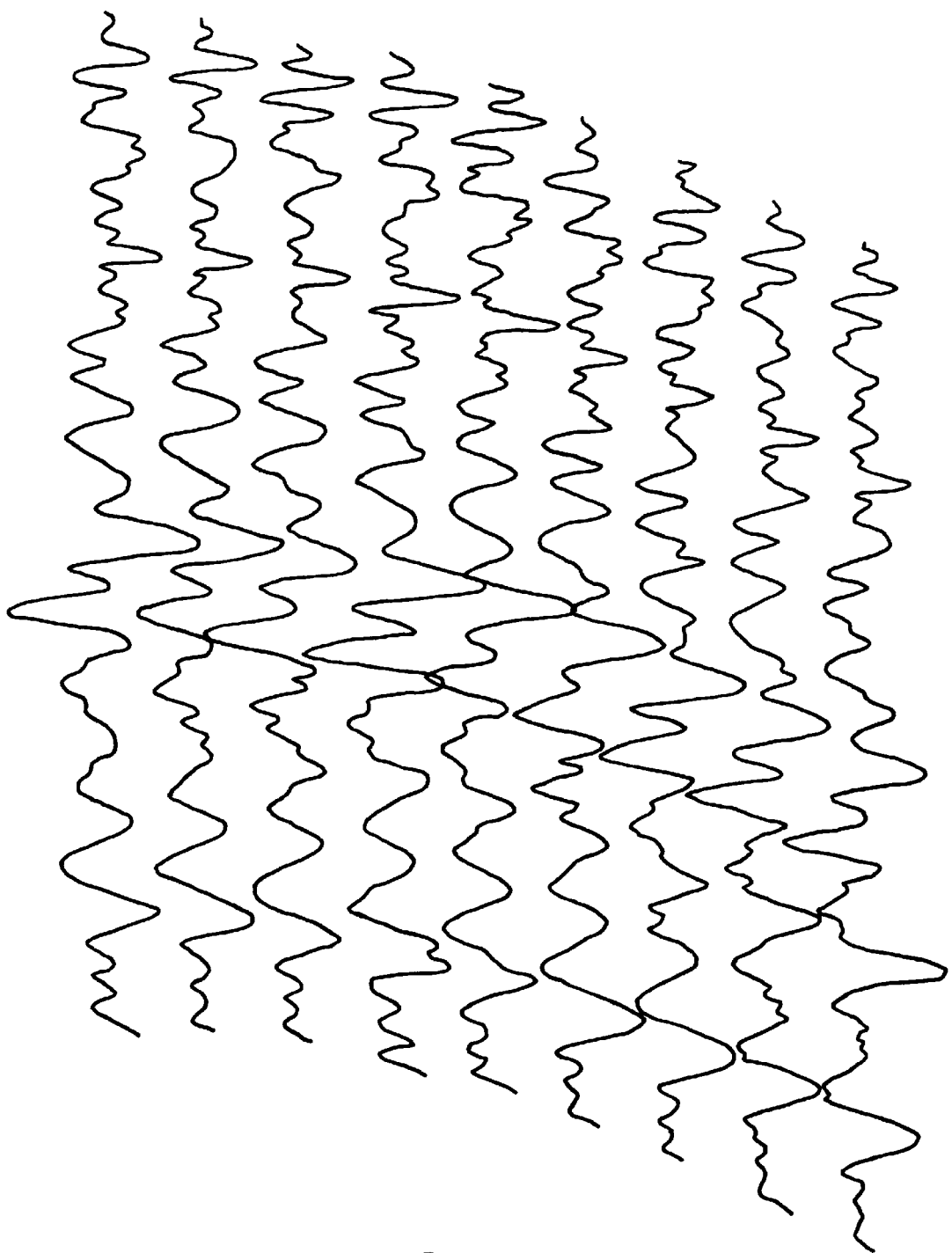
FIG. 4 is a representation of the respective gathers (i.e. recorded signals) from different receivers.
Figure 5:
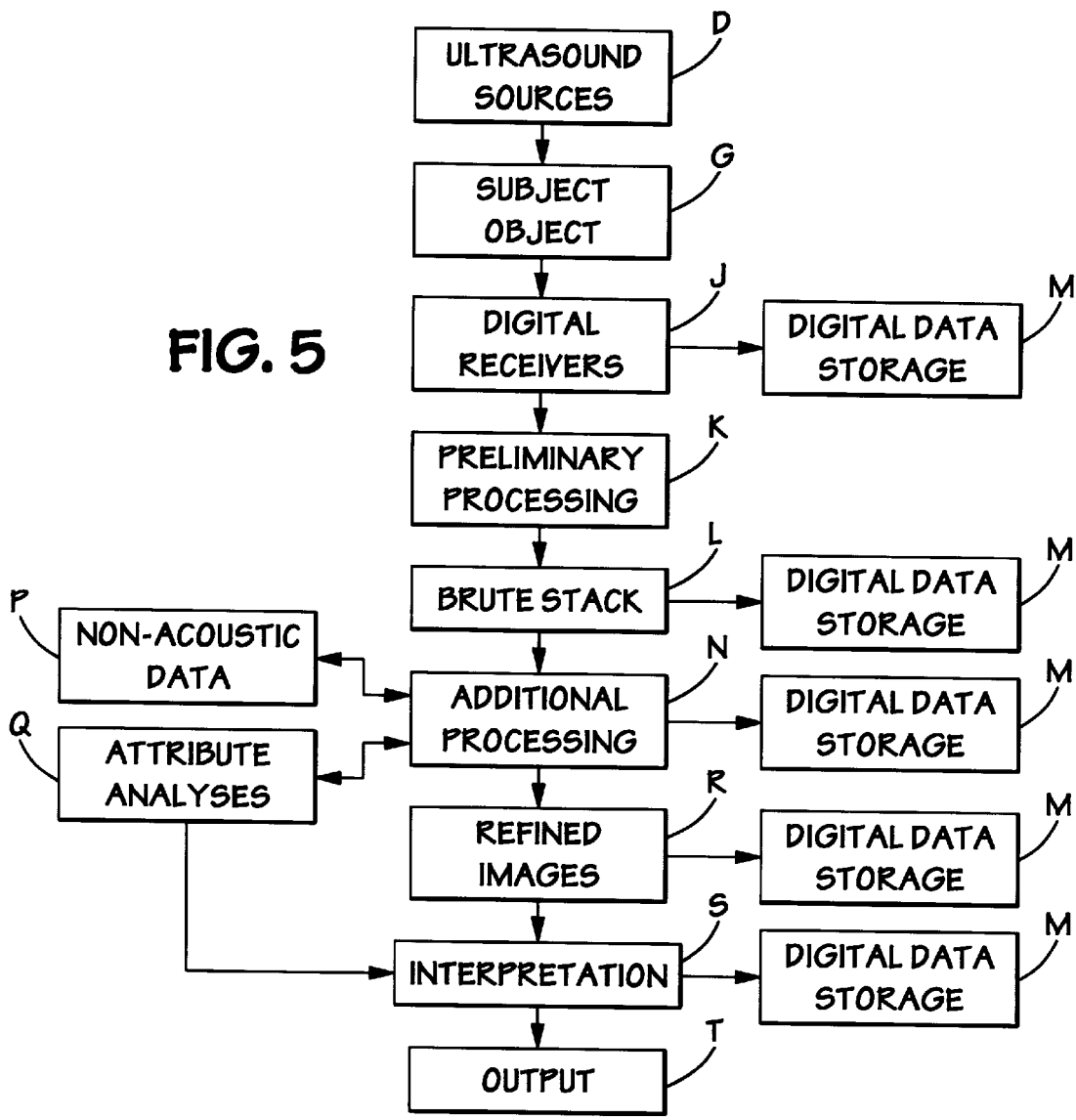
FIG. 5 is a block diagram of the ultrasound imaging system, showing the interactions of the various signal handling functions.

The gathers of FIG. 4 illustrate the recorded traces from each of the ray paths of FIG. 3. The amount of increasing time with increasing offset yields wave propagation velocities for processing and interpretation. Changes in amplitude with offset can, in particular circumstances, yield direct information about fluid/gas status.

Figure 2:
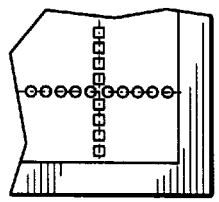
FIG. 2 is a detail representation of a lattice subpanel showing sources and receivers mounted on their supports.

The recorded signals from each receiver are digitally stored in the data handling system (H), which is illustrated in FIG. 2. Data flow in the data handling system is as follows: the signals from the object to be analyzed are collected by the digital receivers (J) and then stored in the Digital Storage system (M) prior to presentation to the preliminary processing circuitry (K). Next, the data are assembled in the Brute Stack (L) and recorded in Digital Storage (M). Data in Storage are either raw data from the Receivers or partially processed date from intermediate manipulations, or final image data. Each type of data are flagged in the storage records. The received data are permanently stored for possible future reprocessing, while intermediate data may also be stored or not after the creation of the Final Image.

Additional Processing (N) prepares data from the Brute Stack, sometimes making use of Non-Acoustic Data (P) and/or Attribute Analyses (Q) to create Refined Images (R), which are then Interpreted (S), sometimes with reference to the Attribute Analyses (Q). The final processing turns the data into final, precisely located images at the Output (T).

Figure 6:
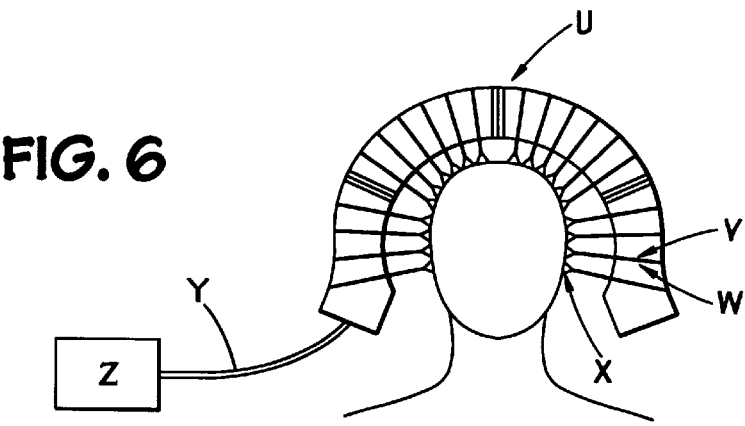
FIG. 6 shows an alternate implementation of the Ultrasound Imaging System of this invention, wherein the sources and receivers constituting the lattice are mounted on the ends of extendable rods which are themselves precisely located in a hard shell support.

An alternate implementation makes use of the same handling system but has a different lattice system. This alternate system is illustrated in FIG. 6. A rigid shell (U) contains numerous rods (V). These rods are moveable in and out of the shell, with the precise amount of travel measured by sensors (W). The rods also have sources and or receivers mounted on the inner end (X), and signal cables (Y) attached to the exterior ends. With both the location of the rod in the shell, and the degree of rod extension known, the source and receiver positions can be precisely calculated. The signals cables are gathered into a signal bundle (Z) which is the same as (F) in FIG. 1. In this implementation, the system is able to make use of shear waves (which cannot travel through a liquid) in the analysis. The rigid-shell lattice is also be composed of interlocking, replaceable components.

The invention may be embodied in other specific forms without departing from the spirit or essential characteristics thereof. The present embodiments should be considered in all respects as illustrative and are not restrictive, with the scope of the invention being indicated by the appended claims, and all the changes that come within the meaning and range of equivalency of the claims are intended to be embraced therein.

I claim:

1. An ultrasound imaging system for observing the interior and exterior details of an object placed within the field of said imaging system, comprising:

a plurality of ultrasound signal sources, emitting a plurality of ultrasound signals, said signals comprising compression-wave and shear-wave energy components;

a plurality of ultrasound signal receivers, said receivers separated from said sources, said receivers adapted to receive said signals, said signals interacting with a plurality of details of said object, said interactions comprising a plurality of reflections and refractions;

a control system, which controls said sources and said receivers, said control system further controlling manipulation and presentation of data from said receivers.

2. The ultrasound imaging system of claim 1 wherein, each of said sources is independently tunable in one or more of the parameters: frequency, duration, phase, and amplitude.

3. The ultrasound imaging system of claim 1 wherein said sources and said receivers are mounted in a defined geometrical lattice; positions of said sources and said receivers being precisely known within said lattice.

4. The ultrasound imaging system of claim 3, wherein said lattice comprises a plurality of sections, each of which contain said sources and said receivers in fixed locations; said sections being interchangeable and reconfigureable.

5. The ultrasound imaging system of claim 3, wherein said control system is a programmable digital computer.

6. The ultrasound imaging system of claim 3, wherein said control system is connected to a digital data recording instrumentality which records and saves the signal from each of said receivers in a distinct record.

7. The ultrasound imaging system of claim 3 wherein said control system is a programmable digital computer programmed to control said sources to create a shaped wavefront to illuminate selectively any portion of the effective area of said lattice.

8. The ultrasound imaging system of claim 6, wherein said control system is a programmable digital computer which further processes said saved signal data to extract said details of any portion of said object placed within said lattice.

9. The ultrasound imaging system of claim 6, wherein said computer defines a Cartesian coordinate system within said object and determines an origin (0,0,0 point) for said coordinate system.

10. The ultrasound imaging system of claim 8, wherein said computer analyses said recorded signal data by imposing an initial estimate for the structural details, the densities, and the wave propagation velocities of said object.

11. The ultrasound imaging system of claim 6, wherein a plurality of markers of known acoustic absolute impedance are affixed to the surface of and/or introduced internally to said object.

12. The ultrasound imaging system of claim 3, wherein said lattice comprises a rigid shell with each of said sources and said receivers mounted on the first end of a rod; said rods penetrating through said shell; the distance of each penetration being precisely measured by a sensor; the second end of said rod connected to said control system; said rods then adjusted in said length of penetration until said first ends come into direct contact with said object.

13. The ultrasound imaging system of claim 3, wherein a plurality of markers having known reflection coefficient are affixed to said surface or introduced within said object.

14. A method of ultrasound imaging comprising placing an object to be imaged in an imaging system comprising:
   a plurality of ultrasound signal sources, emitting a plurality of ultrasound signals,
   said signals comprising compression-wave and shear-wave energy components;
   a plurality of ultrasound signal receivers,
      said receivers separated from said sources,
      said receivers adapted to receive said signals,
      said signals interacting with a plurality of details of said object,
      said interactions comprising a plurality of reflections and refractions;
   a control system, which controls said sources and said receivers,
      said control system further controlling manipulation and presentation of data from said receivers;
   said object being subjected to a plurality of ultrasound signals from said sources passing through said object and received by said receivers, that in turn are processed by said control system to provide a presentation of said received signals representing a three-dimensional image of said object.

15. The method of claim 14 wherein said sources and said receivers are mounted on a defined geometrical lattice which is immersed in a liquid having known reflection coefficient with said object, said object being moved into said liquid for imaging.

16. The method of claim 14 wherein said sources are activated by said control system to provide a wave of sonic energy which is focused in strength and position within the field of said sources.

17. The method of claim 14 wherein said control system defines a Cartesian coordinate system within the object to aid in interpretation of said signals.

18. The method of claim 14 wherein markers of known reflection coefficient are affixed to the surface of or internal portions of said object to aid in determining acoustic impedance within said object.

19. The method of claim 14 wherein said received signals are saved and later reprocessed to extract details of said object not analyzed as part of the original analysis of said signals.

20. The method of claim 17, wherein data from subsequent imaging sessions of said object are analyzed and compared to said image from previous imaging sessions to observe changes in said details of said object.

* * * * *